United States Patent
Elliott

Patent Number: 5,226,536
Date of Patent: Jul. 13, 1993

[54] DISPENSING HOLDER FOR DENTAL ABRASIVE DISCS

[76] Inventor: Gregory E. Elliott, 34441 W. Eight Mile Rd., Ste. 114, Livonia, Mich. 48152

[21] Appl. No.: 869,169

[22] Filed: Apr. 16, 1992

Related U.S. Application Data

[63] Continuation-in-part of Ser. No. 670,016, Mar. 15, 1991, abandoned.

[51] Int. Cl.⁵ .................. B65D 83/04; B65D 85/02
[52] U.S. Cl. ................... 206/369; 206/303; 206/368; 206/445; 206/486; 312/209; 433/77
[58] Field of Search ............ 206/303, 309, 368, 369, 206/372, 445, 486; 211/59.1, 59.2, 49.1; 312/45, 72, 209; 433/77

[56] References Cited

U.S. PATENT DOCUMENTS

| | | |
|---|---|---|
| 282,385 | 7/1883 | Shepard ............... 206/303 |
| 781,313 | 1/1905 | Thomas . |
| 1,086,409 | 2/1914 | Smith . |
| 1,193,203 | 8/1916 | Taliaferro . |
| 1,659,315 | 2/1928 | Dailey . |
| 2,281,237 | 4/1942 | Eckman ............... 206/445 X |
| 2,810,243 | 10/1957 | Mellower ............. 206/303 X |
| 3,047,144 | 7/1962 | Wissel ................. 206/445 X |
| 3,053,384 | 9/1962 | Loomis ................ 206/372 |
| 3,270,416 | 9/1966 | Massa . |
| 3,393,798 | 7/1968 | Beers .................. 206/372 |
| 3,451,133 | 6/1969 | Hathaway et al. . |
| 3,630,349 | 12/1971 | Reehberger .......... 206/372 |
| 4,226,329 | 10/1980 | Knight . |

*Primary Examiner*—Bryon P. Gehman
*Attorney, Agent, or Firm*—Charles W. Chandler

[57] ABSTRACT

A holder for supporting dental discs in a position such that the spindle of a rotary drill can be inserted through the center of the disc in order to pick up the disc without manipulating the disc with the user's hands. The holder has a notch and storage area for removing the used disc from the spindle.

19 Claims, 2 Drawing Sheets

DISPENSING HOLDER FOR DENTAL ABRASIVE DISCS

CROSS REFERENCE TO RELATED PATENT APPLICATION

This is a continuation-in-part of my copending patent application, Ser. No. 670,016, filed Mar. 15, 1991, now abandoned.

BACKGROUND AND SUMMARY OF THE INVENTION

This invention is related to a holder for supporting at least one dental abrasive disc so that it can be picked up by inserting the tip a drill head spindle through the central aperture in the disc.

Dental abrasive discs are only about ½ inch in diameter, and are composed of a thin, abrasive material. A disk is difficult to pick up with the user's fingers and to mount on the drill head spindle.

Dental tool dispensing devices are known in the prior art which, for example, permit a dentist to replace the burr in his drill while using only one hand for the procedure. Such a device is illustrated in U.S. Pat. No. 3,270,416 which was issued Sep. 6, 1966 to Anthony Massa. Another dispensing holder for facilitating the insertion and removal of a dental burr is illustrated in U.S. Pat. No. 3,451,133 which was issued Jun. 24, 1969 to D. B. Hathaway and I. E. Henry.

A sanitary receptacle for holding broaches, burrs and various other articles is illustrated in U.S. Pat. No. 1,659,315 which was issued Feb. 14, 1928 to Frank L. Dailey.

U.S. Pat. No. 1,193,203 which was issued Aug. 1, 1916, to S. W. Taliaferro, discloses a magazine holder for dental abrasive discs.

U.S. Pat. No. 781,313 which was issued Jan. 31, 1905 to Jacob A. Thomas, discloses a dental disc package for supporting a stack of discs.

U.S. Patent No. 1,086,409 which was issued to J. J. Smith, discloses a shipping container for abrasive disks. The container has several circular, column-like compartments that are closed by a flat cover; apparently the cover is removable. The abrasive disks are stacked on holders that include upstanding rods adapted to extend through central holes in the disks. With the cover removed, the individual holders are lowered into the individual compartments or lifted out of the compartments. The shipping container can be used to display the abrasive disks at the point of sale.

U.S. Pat. No. 4,226,329 which was issued to David Knight on Oct. 7, 1980, discloses a stacking device for sanding discs used in paint shops. Presumably the patentee contemplates using the stacking device in automobile body repair facilities where automobiles are sanded prior to being repainted. The device disclosed in the patent comprises an upstanding cylindrical container mounted on a flat circular base, whereby a large number of circular sanding discs can be stacked for easy access by the mechanic equipped with a rotary sanding machine. The patentee indicates that by stacking the discs in the container, the discs are at least partially protected against the shop dust while being available as needed. Apparently the repairman can extract the uppermost disc in the stack from the container by moving a sanding wheel downwardly within the container so that its adhesive surface comes in contact with the exposed surface of the topmost sanding disc.

A principal aim of the invention disclosed in U.S. Pat. No. 4,226,329 is apparently to house a large number of sanding discs in a single stack so that the individual discs are shielded from shop dust while being available to the auto body repairman, as needed.

SUMMARY OF THE INVENTION

The broad purpose of the present invention is to provide a tray or holder for supporting individual dental polishing and abrasive discs. The tray has a body with three circular recesses, each for receiving a disc having different abrasive characteristics The drill head spindle has a split, resilient end, the tip of which has a circumferential groove adjacent the terminal end of the spindle. Each recess in the holder has a resilient disc support surface so the user can insert the spindle through an aperture in the center of the disc into the resilient support surface such that the disc then snaps on the spindle. When the polishing procedure is completed, the dentist or dental technician inserts the disc into a storage pocket in the body of the holder and removes the disc by pulling the spindle away from the holder; the storage pocket has structure for retaining the disc.

In another embodiment of the invention, the holder is of a relatively non-resilient, disposable material, but the disc support surface in each circular recess has a blind socket centrally located therein. The dentist inserts the spindle into the disc by passing the spindle tip downwardly through the disc and into the blind socket in the disc support surface.

In this embodiment, the tip of the spindle is received into the blind socket sufficiently for the disc to snap on the spindle. The depth of the blind socket can be selected such that when the terminal end of the spindle contacts the bottom of the socket, the circumferential groove is substantially aligned with the plane of the disc. This guarantees proper positioning of the disc on the spindle tip.

The preferred holder permits the dentist to easily insert and remove a single individual disc without handling the disc. The holder is convenient to use, obviates the problems of picking up a relatively small, thin object and provides sanitary means for disposing of the used disc.

Still further objects and advantages of the invention will become readily apparent to those skilled in the art to which the invention pertains upon reference to the following detailed description.

DESCRIPTION OF THE DRAWINGS

The description refers to the accompanying drawings in which like reference characters refer to like parts throughout the several views, and in which.

DESCRIPTION OF A PREFERRED EMBODIMENT OF THE INVENTION

Figure 1:
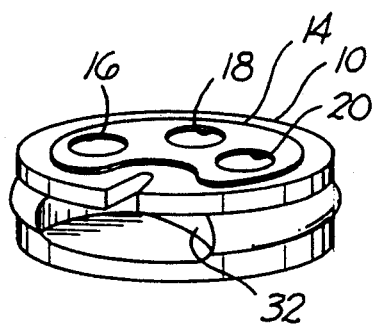
FIG. 1 is a perspective view of a dental abrasive disc holder illustrating a first preferred embodiment of the invention.

Referring to the drawings, FIGS. 1-4 illustrate holder 10 which is formed of a relatively hard, sterilizable plastic material. Holder 10 comprises a circular holder body having a generally circular configuration, and a vertical thickness of about ⅛ inch.

Figure 3:
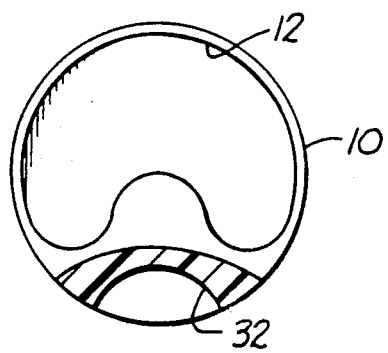
FIG. 3 is a partially fragmentary view of the holder of FIG. 1 with the disc-supporting insert removed.
Figure 4:
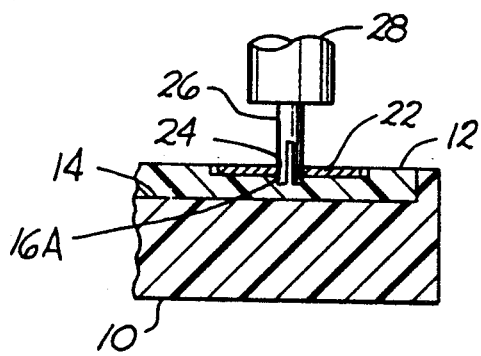
FIG. 4 is a sectional view of the holder showing the drill spindle being inserted into a disc.

As best illustrated in FIGS. 3 and 4, the top surface of the holder body has a kidney-shaped cavity 12.

A resilient elastomeric insert 14 is permanently seated in cavity 12 and has a thickness corresponding to the depth of cavity 12. The border of insert 14 coincides with the border of cavity 12.

Insert 14, for illustrative purposes, has three circular recesses 16, 18 and 20, each about ½ inch in diameter and ⅛ inch in depth. Each circular recess is intended to receive therein a dental abrasive disc having a different abrasive or polishing surface. Usually, the dentist will progress through discs of different polishing characteristics as he progresses through the patient's treatment. The base of recesses 16, 18 and 20 have smaller, centrally located, blind socket openings 16A, 18A, and 20A, respectively. "Blind socket" and "blind socket opening" as used herein refer to a hole formed in a body in which the only entrance is from one surface of the body. That is, the hole does not extend completely through the body. For instance, sockets 16A, 18A, and 20A open only into recesses 16, 18, and 20, respectively.

Figure 5:
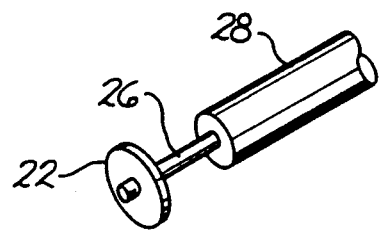
FIG. 5 is a view showing the disc mounted on the drill head spindle.

The circular recesses are designed to each receive a typical circular dental disc of the type generally illustrated at 22. The disc has a central aperture 24. A representative disc has a diameter such that when seated within its respective recess, central aperture 24 is disposed over socket opening 16A, as shown in FIG. 4. Socket opening 16A is designed to receive the spindle 26 of a conventional dental drill head 28. It is to be understood that if the insert material 14 is sufficiently resilient, there may not be a need for socket opening 16A. Socket opening 16A permits the user to press the spindle end into the insert material to a depth sufficient to snap the disc on the spindle. In order to operatively (firmly) attach the disc to the spindle, the spindle must extend completely through and beyond the disc plane, as shown in FIGS. 4 and 5.

As is well known, a conventional, commercial spindle has a tubular end with a split construction. The spindle diameter becomes somewhat reduced as it passes through the disc aperture until the disc is operatively seated on the spindle. In this embodiment of the invention, the spindle can be readily inserted into the disc without manipulating the disc.

Figure 2:
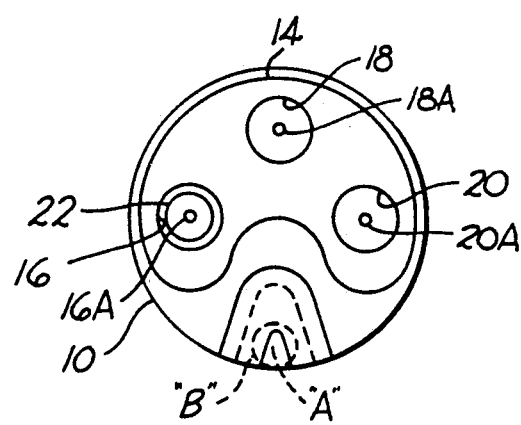
FIG. 2 is a plan view of the holder in FIG. 1.

Referring to FIGS. 1 and 2, body 10 has a pocket 32 in the side edge of the body. Pocket 32 is shown as an arcuate slot formation in the edge of body 10. The slot is substantially larger than the diameter of the disc. For example the slot may extend into the holder body by about ⅜ of an inch.

The roof of pocket 32 has a notch 34 that extends from the edge of the holder inwardly into communication with pocket 32. The roof has a thickness less than the distance between the disc and the drill head and the notch has a width greater than the spindle diameter but less than the diameter of the abrasive disc. Thus, the user can insert the spindle to a position generally as illustrated in phantom at "A" in FIG. 2, in which the disc is received in pocket 32, to a position illustrated in phantom at position "B". The disc is removed by pulling the spindle away from the holder as the disc engages the inner surface of the roof of pocket 32. This permits the disc to be removed from the spindle without the dentist using his fingers to grasp the disc. The notched roof of pocket 32 constitutes a retainer device for retaining an abrasive disc within the pocket; the retainer mechanism could be a separate bracket mounted on the holder body overlying the pocket.

Figure 6:
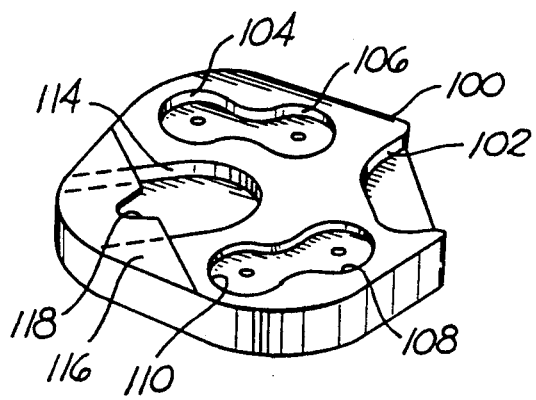
FIG. 6 is a view of another preferred embodiment of the invention in which the disc-removing notch is mounted on top of the holder.
Figure 7:
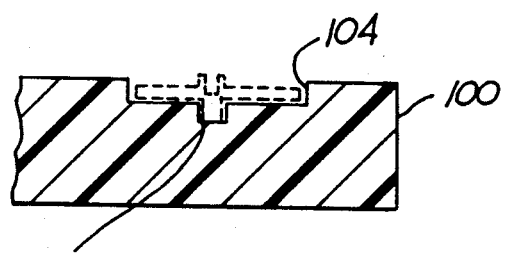
FIG. 7 is a sectional view through the embodiment of FIG. 6.
Figure 8:
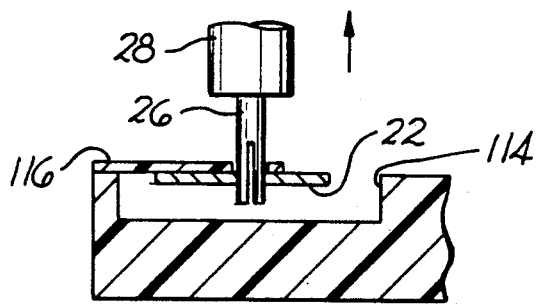
FIG. 8 is a view illustrating the disc being removed by the notch of the embodiment of FIG. 6.

Referring to FIGS. 6-8, a disposable holder 100 is formed of a suitable, disposable plastic material. Holder 100 has a thickness of about ¼ inch, and a recess 102 for the user to grip the holder. The holder has plurality of generally circular recesses 104, 106, 108 and 110 for receiving individual discs of different polishing characteristics. Each recess is about ⅛ inch deep and suited to receive an individual disc. Each circular recess also has a blind socket opening 112, formed in its bottom surface, as illustrated in FIG. 7.

Socket opening 112 has a depth that is greater than the projecting portion of the spindle tip so that the tip can be fully received in the central socket opening as the spindle is being inserted in the central aperture of the disc.

Alternatively, the blind socket opening could have a limited depth such that when a drill head spindle is inserted downwardly through the aperture in an abrasive disc into the associated socket opening, the spindle movement is limited to a point where the disc is operatively attached to the spindle.

The top surface of holder 100 also has a pocket 114 with a depth and diameter sufficient to hold several discs; as shown in FIG. 8, the pocket is formed by a depression in the upper surface of the holder body. A top wall or roof structure extends across a part of the top edge of pocket 114 to define an opening sufficient for the user to insert the disc into pocket 114 to a location beneath roof structure 116. Roof structure 116 has a notch 118 having a width greater than that of the diameter of spindle 26 but less than the diameter of disc 22. The dentist can insert the spindle into notch 118 and remove the disc by pulling the spindle upwardly away from the holder 100. The separated disc remains in the pocket 114.

Pocket 114 has a sufficient capacity to store all the discs after they have been used. Then the entire holder and spent discs can be disposed of in the customary manner.

Figure 9:
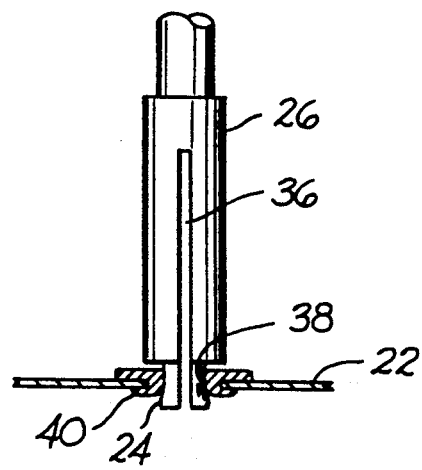
FIG. 9 is an enlarged sectional view through a representative dental abrasive disc, showing the disc attached to the spindle of a dental instrument.

FIG. 9 shows in greater detail the relation between a representative sanding disc 22 and the spindle of the dental machine. The spindle has two crossed slots extending longitudinally therealong to give the spindle some transverse (radial) resiliency. One of the longitudinal slots is shown at 36 in FIG. 9. Also, the spindle has a circumferential groove 38 at its lower (terminal) end adopted to receive the abrasive disc thereon.

As shown in FIG. 9, the abrasive disc has a grommet 40 thereon defining the aforementioned central aperture 24. Socket openings 16A, 18A and 20A each have a diameter greater then that of the opening in grommet 40, but smaller than the major diameter of the grommet, such that when the abrasive disc is resting on the flat bottom surface of an associated recess 16, 18 or 20, the rigid grommet is in contact with the surface of the recess. The hole in grommet 40 can be circular, square or octagonal; the grommet hole does not necessarily have to have the same cross-sectional shape as the spindle.

A dentist or dental technician attaches an abrasive disc 22 to the spindle 26 by manipulating the head of the dental machine so that the spindle is forced downwardly through the hole in grommet 40. The reduced end portion of the spindle is passed through the grommet hole into the blind socket opening therebelow while the grommet is supported by the surface of the associated recess 16, 18 or 20. The spindle is somewhat resilient (due to slots 36) such that the surface of spindle groove 38 has a good frictional engagement with the grommet surface, whereby the abrasive disc is prevented from slipping on the spindle.

Each of the illustrated embodiments includes a notched wall structure overlying a disc storage pocket to enable an abrasive disc to be dislodged from a drill head spindle into the pocket. The notched wall structure in each case acts as a retainer device for the abrasive disc.

Typically, dental polishing discs have relatively small central apertures 24 therein. For example, the aperture in grommet 40 (FIG. 9) typically has a diameter of only about 0.08 inch. The task of inserting an abrasive onto the spindle of a dental machine spindle without handling the disc is not easily accomplished. However, by positioning each individual disc in an individual recess 16, 18, 20, 104, 106, 108 or 110, the task is accomplished without too much difficulty. By making the floor surface of each recess resilient and/or by forming a socket opening in each floor surface, the process is greatly facilitated because the grommet portion of the disc is adequately supported while the spindle is allowed to completely penetrate the central hole in the disc (grommet). It is necessary that the spindle extend completely through and beyond the disc plane, as shown in FIGS. 4, 5 and 9; otherwise the polishing disc may slip off the spindle when the spindle begins to rotate.

The disc storage pocket 32 or 114 is believed to be an advance in the art, in that it enables the dentist or dental technician to automatically separate the disc from the spindle. The person's hand or glove is thus not subject to being cut or scratched by the sharp edge of the disc, as might be the case if the person were required to manually handle the disc in order to separate the disc from the spindle.

The invention teaches a relatively small compact holder structure for a plural number of small abrasive dental disks, whereby the dentist or dental technicians can automatically attach a selected disc to a dental machine spindle or remove a disc from the spindle. The holder structure can be placed on a tray in front of the dentist while he/she is performing a teeth polishing operation on a patient.

Each disc-receiving recess 16, 18, 20, 104, 106, 108 or 110 is adapted to receive only a single abrasive disc. The disc is supported in a relatively stable position wherein the dentist can easily pilot the spindle downwardly through central grommet 40, to attach the disc to the spindle. The arrangement differs substantially from the arrangement of the aforementioned U.S. Pat. No. 4,226,329 issued to D. Knight. The Knight arrangement would not be practical in a dental disc environment because it would be very difficult for the dentist to see the central grommet in the topmost disc when the topmost disc was in a depressed position below the upper edge of the container; piloting of the spindle into the grommet hole would be quite difficult. Also, the disc grommet thickness would prevent the discs from lying in stable flat positions in the container.

The present invention contemplates a disc holder construction wherein individual abrasive discs of different abrasive fineness are individually supported in shallow recesses in the holder body, whereby a dentist or dental technician ca readily select and attach any one of the discs to a dental spindle without physically handling the disc.

Having described my invention, I claim:

1. A dental disc holder for supporting at least one generally planar dental disc having a centrally located aperture therethrough for pick-up by the circumferentially grooved tip of a longitudinally slotted, radially flexible spindle end of a dental instrument, said holder comprising:
    body means for holding at least one dental disc, said body means having an upper surface;
    at least one blind recess formed in said upper surface for retaining a dental disc, each recess having a depth sufficient to retain only one dental disc below said upper surface;
    each blind recess including means for preventing substantial movement of a retained said dental disc downwardly into the recess when a said spindle end is force-fit into the aperture; and
    each recess further including means for permitting a said spindle tip to extend beneath the plane of the retained dental disc at least sufficiently to align the plane with the circumferentially grooved tip.

2. The holder of claim 1 wherein said means for preventing substantial movement comprises each recess having a substantially flat, rigid bottom surface, and said means for permitting comprises a blind socket in each recess bottom surface.

3. The holder of claim 2 wherein said at least one recess comprises a plurality of similar recesses spaced laterally adjacent one another in said upper surface.

4. The holder of claim 2 wherein each blind socket has a limited depth such that when the spindle end is in contact with the bottom surface of the blind socket, the circumferential groove of the tip substantially aligns with the plane of the retained disc.

5. The holder of claim 1 wherein said body means further includes disc removal means for removing a disc from the spindle end, said removal means being operative to remove the disc from the spindle end without the need for touching the disc.

6. The holder of claim 5 wherein said removal means comprises a pocket having an entrance opening, an overhanging roof, and a notch in said roof, said notch opening into said entrance opening.

7. The holder of claim 6 wherein said notch has a width smaller than the diameter of a disc on the spindle end and larger than the diameter of the spindle end.

8. The holder of claim 1 wherein said at least one recess comprises a plurality of similar recesses spaced laterally adjacent one another in said upper surface.

9. The holder of claim 8 wherein said plurality of recesses are individually adapted to receive discs of respectively differing characteristics.

10. The holder of claim 8 wherein said body means further includes disc removal means for removing a disc from the spindle end, said removal means being operative to remove the disc from the spindle end without the need for touching the disc.

11. The holder of claim 10 wherein said removal means comprises a pocket having an entrance opening, an overhanging roof, and a notch in said roof, said notch opening into said entrance opening.

12. The holder of claim 11 wherein said notch has a width smaller than the diameter of a disc on the spindle end and larger than the diameter of the spindle end.

13. The holder of claim 11 wherein said body means comprises a rigid body portion having a cavity formed therein, a resilient insert fitted within said cavity, and said upper surface and each blind recess comprising portions of said resilient insert.

14. The holder of claim 13 wherein said cavity includes a substantially rigid, flat bottom and said means for preventing substantial movement comprises said resilient insert being supported by the cavity bottom.

15. The holder of claim 14 wherein said means for permitting said spindle tip to extend beneath said dental disc plane comprises a blind socket in said recess bottom surface.

16. The holder of claim 14 wherein said means for permitting consists solely in the resiliency of said insert.

17. The holder of claim 13 wherein said body means further includes a disc removal means for removing a disc from the spindle end, said removal means being operative to remove the disc from the spindle end without the need for touching the disc.

18. The holder of claim 17 wherein said removal means comprises a pocket having an entrance opening, an overhanging roof, and a notch in said roof, said notch opening into said entrance opening.

19. The holder of claim 18 wherein said notch has a width smaller than the diameter of a disc on the spindle end and larger than the diameter of the spindle end.

* * * * *